United States Patent
Eggen et al.

(10) Patent No.: US 12,059,558 B2
(45) Date of Patent: Aug. 13, 2024

(54) SHIELD OPTIMIZATION FOR MAXIMIZING HEAT DISSIPATION AT THE DEVICE TISSUE INTERFACE AND IMPROVING FIXATION

(71) Applicant: Medtronic, Inc., Minneapolis, MN (US)

(72) Inventors: Michael D. Eggen, Chisago City, MN (US); Yong K. Cho, Excelsior, MN (US); D'anne E. Kudlik, Saint Louis Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 1021 days.

(21) Appl. No.: 16/885,363

(22) Filed: May 28, 2020

(65) Prior Publication Data
US 2020/0384174 A1    Dec. 10, 2020

Related U.S. Application Data

(60) Provisional application No. 62/858,374, filed on Jun. 7, 2019.

(51) Int. Cl.
| | |
|---|---|
| *A61M 60/876* | (2021.01) |
| *A61M 60/178* | (2021.01) |
| *A61M 60/232* | (2021.01) |
| *A61M 60/237* | (2021.01) |
| *A61M 60/422* | (2021.01) |
| *A61M 60/50* | (2021.01) |
| *A61M 60/873* | (2021.01) |

(52) U.S. Cl.
CPC .......... *A61M 60/50* (2021.01); *A61M 60/178* (2021.01); *A61M 60/232* (2021.01); *A61M 60/237* (2021.01); *A61M 60/422* (2021.01); *A61M 60/873* (2021.01); *A61M 60/876* (2021.01); *A61M 2205/0233* (2013.01); *A61M 2205/8206* (2013.01)

(58) Field of Classification Search
CPC ......... A61M 1/10; A61M 1/12; A61M 60/876
See application file for complete search history.

(56) References Cited

U.S. PATENT DOCUMENTS

| | | |
|---|---|---|
| 7,997,854 B2 | 8/2011 | LaRose et al. |
| 8,419,609 B2 | 4/2013 | Shambaugh, Jr. et al. |
| | (Continued) | |

FOREIGN PATENT DOCUMENTS

| | | |
|---|---|---|
| CN | 105268103 A | 1/2016 |
| WO | 2013090302 A1 | 6/2013 |
| WO | 2017040317 A1 | 3/2017 |

OTHER PUBLICATIONS

International Search Report and Written Opinion dated Sep. 4, 2020, for corresponding International Application No. PCT/US2020/035047; International Filing Date: May 29, 2020 consisting of 9 pages.

(Continued)

*Primary Examiner* — Matthew W Schall
(74) *Attorney, Agent, or Firm* — Shumaker & Sieffert, P.A (57) ABSTRACT

A controller for an implantable medical device including a housing sized and configured to be received within a patient, the housing having a thermally conductive shell defining an exterior surface. At least a portion of the exterior surface of the thermally conductive shell defines at least one from the group consisting of a plurality of corrugations and a plurality of protuberances.

20 Claims, 5 Drawing Sheets

(56) References Cited

U.S. PATENT DOCUMENTS

| | | |
|---|---|---|
| 8,961,387 B2 | 2/2015 | Duncan |
| 9,560,787 B2 | 1/2017 | Kallmyer et al. |
| 9,680,310 B2 | 6/2017 | Wong et al. |
| 10,148,126 B2 | 12/2018 | Hoarau et al. |
| 2005/0075694 A1 | 4/2005 | Schmeling et al. |
| 2006/0194025 A1 | 8/2006 | Oxenknecht |
| 2007/0255349 A1 | 11/2007 | Torgerson et al. |
| 2011/0190669 A1 | 8/2011 | Mi et al. |
| 2013/0197608 A1 | 8/2013 | Eiger |
| 2017/0250575 A1 | 8/2017 | Wong et al. |
| 2019/0076587 A1 | 3/2019 | Rudser et al. |

OTHER PUBLICATIONS

First Office Action and Search Report, and translation thereof, from counterpart Chinese Application No. 202080043246.0 dated Jan. 10, 2024, 14 pp.

SHIELD OPTIMIZATION FOR MAXIMIZING HEAT DISSIPATION AT THE DEVICE TISSUE INTERFACE AND IMPROVING FIXATION

CROSS-REFERENCE TO RELATED APPLICATION

This application claims the benefit of U.S. application Ser. No. 62/858,374 filed Jun. 7, 2019.

FIELD

The present technology is generally related to implantable blood pump controllers, and in particular, exterior surface modifications to an implantable controller to promote tissue ingrowth and heat dissipation.

BACKGROUND

A mechanical circulatory support device (MCSD), such as a left ventricular assist device (LVAD) is an implantable device that is used to assist the functioning of a failing heart. LVADs include a pump that connects the left ventricle to the aorta which pulls blood from the left ventricle and pumps it into the aorta. Transcutaneous energy transfer (TET) systems are used to supply power to MCSDs implanted internally within a human body. An electromagnetic field generated by a transmitting coil outside the body can transmit power across a cutaneous (skin) barrier to a magnetic receiving coil implanted within the body. The receiving coil can then transfer the received power to the implanted MCSD and/or to an implanted controller configured to operate the MCSD.

The implanted controller is sufficiently sized to accommodate one or more batteries and other electronics configured to power the MCSD. Accordingly, the controller is relatively heavy and may migrate toward unwanted locations within the patient over time. Moreover, the controller generates Joule heating that may cause damage to surrounding tissue.

SUMMARY

The techniques of this disclosure generally relate to implantable medical devices.

In one aspect, the present disclosure provides a controller for an implantable medical device including a housing sized and configured to be received within a patient, the housing having a thermally conductive shell defining an exterior surface. At least a portion of the exterior surface of the thermally conductive shell defines at least one from the group consisting of a plurality of corrugations and a plurality of protuberances.

In another aspect, the controller further includes a battery enclosed within the housing, the battery being configured to power the implantable medical device when the controller is connected to the implantable medical device.

In another aspect, the thermally conductive shell defines the plurality of protuberances, and wherein the plurality of protuberances is disposed on an entirety of the exterior surface of the thermally conductive shell.

In another aspect, each of the plurality of protuberances defines a protuberance height and a protuberance diameter, and wherein a ratio of protuberance diameter to protuberance height is at least 2:1.

In another aspect, a density of the plurality of protuberances on the exterior surface of the thermally conductive shell is 3.25 protuberances per $cm^2$.

In another aspect, each of the plurality of protuberances are spaced apart from each and every other one of the plurality of protuberances.

In another aspect, the thermally conductive shell defines the plurality of corrugations, and wherein the plurality of corrugations is disposed on an entirety of the exterior surface of the thermally conductive shell.

In another aspect, each of the plurality of corrugations defines a cross-sectional shape of one from the group consisting of square, rectangular, triangular, and trapezoidal.

In another aspect, each of the plurality of corrugations is contiguous with an adjacent one of the plurality of corrugations.

In another aspect, each of the plurality of corrugations is spaced apart from each and every other one of the plurality of corrugations.

In one aspect, a controller for an implantable blood pump includes a housing sized and configured to be received within a patient, the housing having a thermally conductive shell defining an exterior surface. At least a portion of the exterior surface of the thermally conductive shell defines at least one from the group consisting of a plurality of corrugations and a plurality of protuberances. A battery is disposed within the housing, the battery being configured to power the implantable blood pump when the controller is connected to the implantable blood pump. The housing is configured to electrically couple with an implantable transcutaneous energy transfer coil, the transcutaneous energy transfer coil being configured to power the battery.

In another aspect, the thermally conductive shell defines the plurality of protuberances, and wherein the plurality of protuberances is disposed on an entirety of the exterior surface of the thermally conductive shell.

In another aspect, each of the plurality of protuberances defines a protuberance height and a protuberance diameter, and wherein a ratio of protuberance diameter to protuberance height is at least 2:1.

In another aspect, wherein a density of the plurality of protuberances on the exterior surface of the thermally conductive shell is 3.25 protuberances per $cm^2$.

In another aspect, each of the plurality of protuberances are spaced apart from each and every other one of the plurality of protuberances.

In another aspect, the thermally conductive shell defines the plurality of corrugations, and wherein the plurality of corrugations is disposed on an entirety of the exterior surface of the thermally conductive shell.

In another aspect, each of the plurality of corrugations defines a cross-sectional shape of one from the group consisting of square, rectangular, triangular, and trapezoidal.

In another aspect, each of the plurality of corrugations is contiguous with an adjacent one of the plurality of corrugations.

In another aspect, the thermally conductive shell defines the plurality of protuberances, and wherein the plurality of protuberances is evenly spaced about the exterior surface.

In one aspect, a controller for an implantable blood pump includes a unitary housing sized and configured to be received within a patient. The housing has a thermally conductive metallic shell defining an exterior surface. An entirety of the exterior surface of the thermally conductive metallic shell defines a plurality of protuberances evenly spaced about the exterior surface. Each of the plurality of protuberances is spaced apart from each and every other one of the plurality of protuberances. Each of the plurality of protuberances defines a protuberance height and a protuberance diameter and a ratio of protuberance diameter to protuberance height is at least 2:1. A battery is disposed within the housing and is configured to power the implantable blood pump when the controller is connected to the implantable blood pump. The housing is configured to electrically couple with an implantable transcutaneous energy transfer coil, the transcutaneous energy transfer coil being configured to power the battery.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
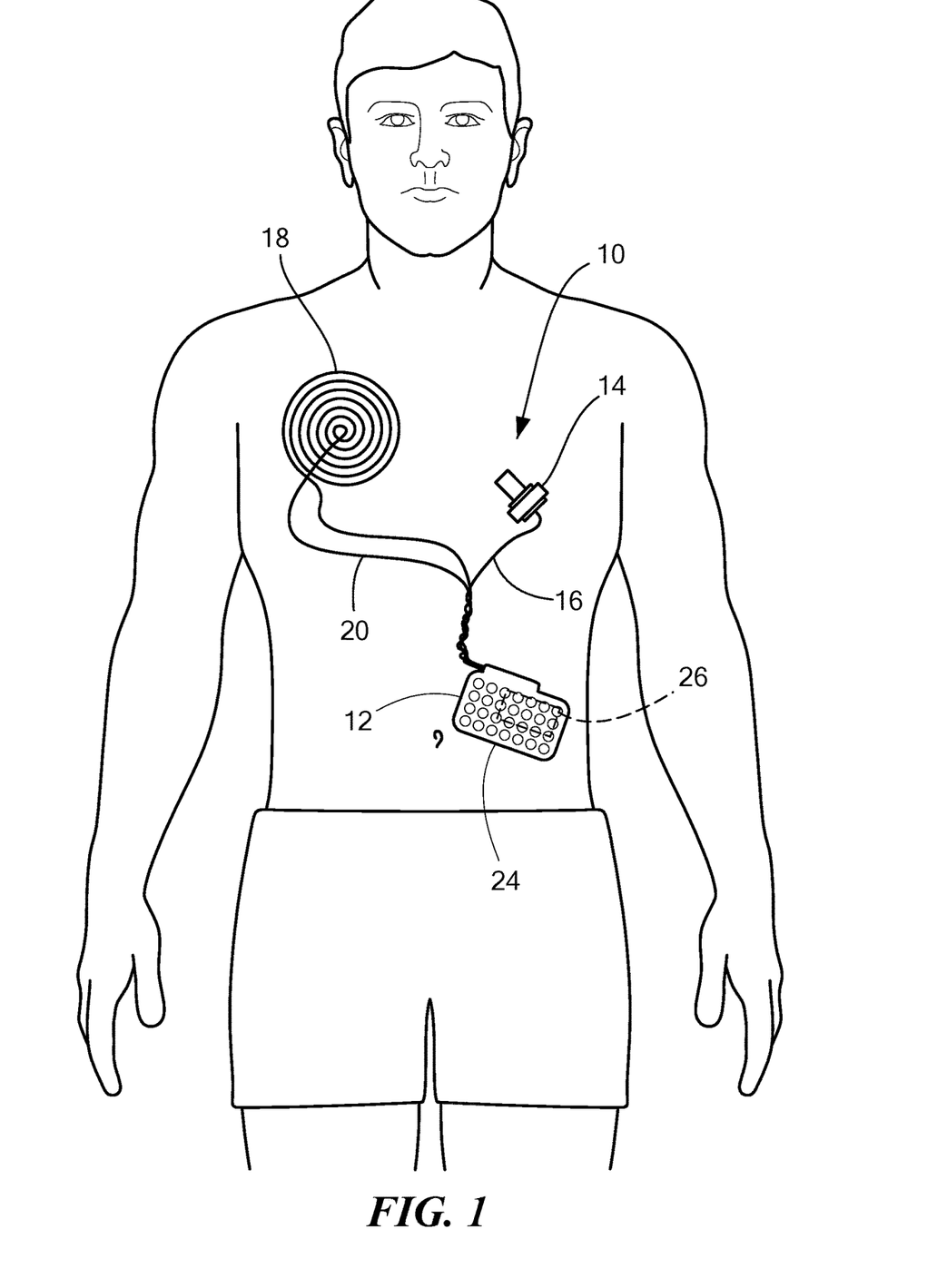
FIG. 1 is a schematic showing an exemplary implantable portion of MCSD system constructed in accordance with the principles of the present application.

Referring now to the drawings in which like reference designators refer to like elements there is shown in FIG. 1 a portion of an exemplary MCSD system constructed in accordance with the principles of the present application and designated generally as "10." The system 10 is fully implantable within a patient, whether human or animal, which is to say there are no percutaneous connections between implanted components of the system 10 and components outside of the body of the patient. In the configuration shown in FIG. 1, the system 10 includes a controller 12 implanted within the body of the patient, for example, within a subcutaneous pocket within the torso surrounded by adipose tissue. The controller 12 may include a battery (not shown) configured to power the components of the controller and provide power one or more implantable medical device, for example, a ventricular assist device (VAD) 14 implanted within the left ventricle of the patient's heart. VADs 14 may include centrifugal pumps, axial pumps, or other kinds electromagnetic pumps configured to pump blood from the heart to blood vessels to circulate around the body. One such centrifugal pump is the HVAD sold by HeartWare, Inc. and is shown and described in U.S. Pat. No. 7,997,854 the entirety of which is incorporated by reference. One such axial pump is the MVAD sold by HeartWare, Inc. and is shown and described in U.S. Pat. No. 8,419,609 the entirety of which is incorporated herein by reference. In an exemplary configuration, the VAD 14 is electrically coupled to the controller 12 by one or more implanted conductors 16 configured to provide power to the VAD 14, relay one or more measured feedback signals from the VAD 14, and/or provide operating instructions to the VAD 14.

Continuing to refer to FIG. 1, a receiving coil 18 may also be coupled to the controller 12 by, for example, one or more implanted conductors 20. In an exemplary configuration, the receiving coil 18 may be implanted subcutaneously proximate the thoracic cavity, although any subcutaneous position may be utilized for implanting the receiving coil 18. The receiving coil 18 is configured to be inductively powered through the patient's skin by a transmission coil (not shown) coupled to an external battery (not shown) disposed opposite the receiving coil 18 on the outside of the patient's body. The receiving coil 18 may be disposed within a hermetically sealed package that does not interfere with the conductivity of the receiving coil 18.

Figure 2:
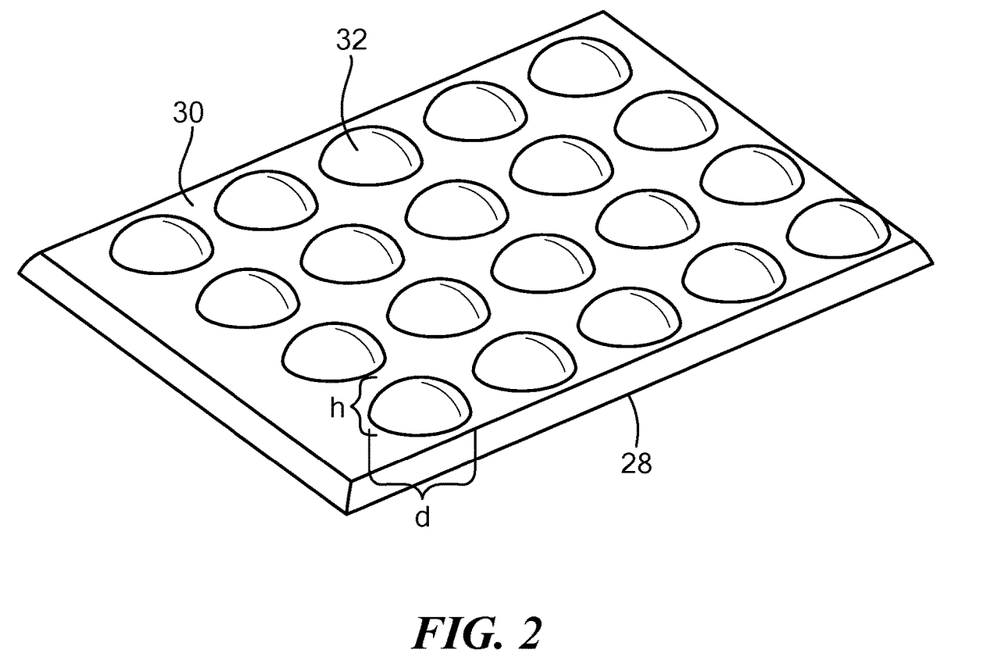
FIG. 2 is a front perspective view of the controller shown in FIG. 1 having exterior surface modifications in accordance with the principles of the present application.

Referring now to FIG. 2, the controller 12 may include a housing 24 defining an interior in which the various electronic components of the controller 12 reside, namely, one or more batteries 26 configured to power the VAD and circuits (not shown) in communication with the VAD 14. The housing 12 includes a thermally conductive shell 28 defining an exterior surface 30. The shell 28 is composed of a thermally conductive and biocompatible material, for example, Titanium, or other biocompatible metals or alloys. In the configuration shown in FIG. 2, the shell 28 encloses the components within the housing 24 and defines a hermetic seal around the controller 12. The exterior surface 30 may define a plurality of protuberances 32 extending a distance away from the shell 28. Any number of protuberances 32 may be included on the exterior surface 30, which may be evenly spaced or unevenly spaced on the exterior surface 30, and in one configuration, the density of protuberances 32 on the exterior surface is 3.25 protuberances per $cm^2$, although any density is contemplated. For example, the protuberances 32 may be disposed on a predetermined portion of the exterior surface 30, or alternatively, may be disposed on the entirety of the exterior surface 28. In one configuration, each protuberance 32 defines a height (h) and a diameter (d) and the ratio of d/h is 2:1. In other configurations, the ration of d/h may be greater than 2:1, for example, 3:1. In one configuration, each protuberance 32 is contiguous with an adjacent protuberance 32, and in other configurations each protuberance 32 may be spaced a distance apart from an adjacent protuberance 32. In one configuration, all the protuberances 32 defines the same shape and size and in other configurations, some of the protuberances 32 may be one shape and size and other protuberances 32 may be another shape and size depending on the location of the controller 12 when implanted. For example, different heat dissipation rates may be desired at different implant locations within the body and the greater the surface area of the exterior surface 30 of the shell 28, which is increased by the protuberances 32, the greater the heat dissipation. Moreover, the protuberances 32 increase tissue fixation surrounding adipose and/or muscle tissue to prevent unwanted migration, either by increasing the amount of friction at the device tissue interface or by the chronic ingrowth of fibrous tissue around the protuberances 32. In one configuration, the protuberances 32 are composed of the same material as the shell 28, and in other configurations, may be composed of a different thermally conductive material than the shell 28, for example, a different metal or metal alloy.

Figure 3:
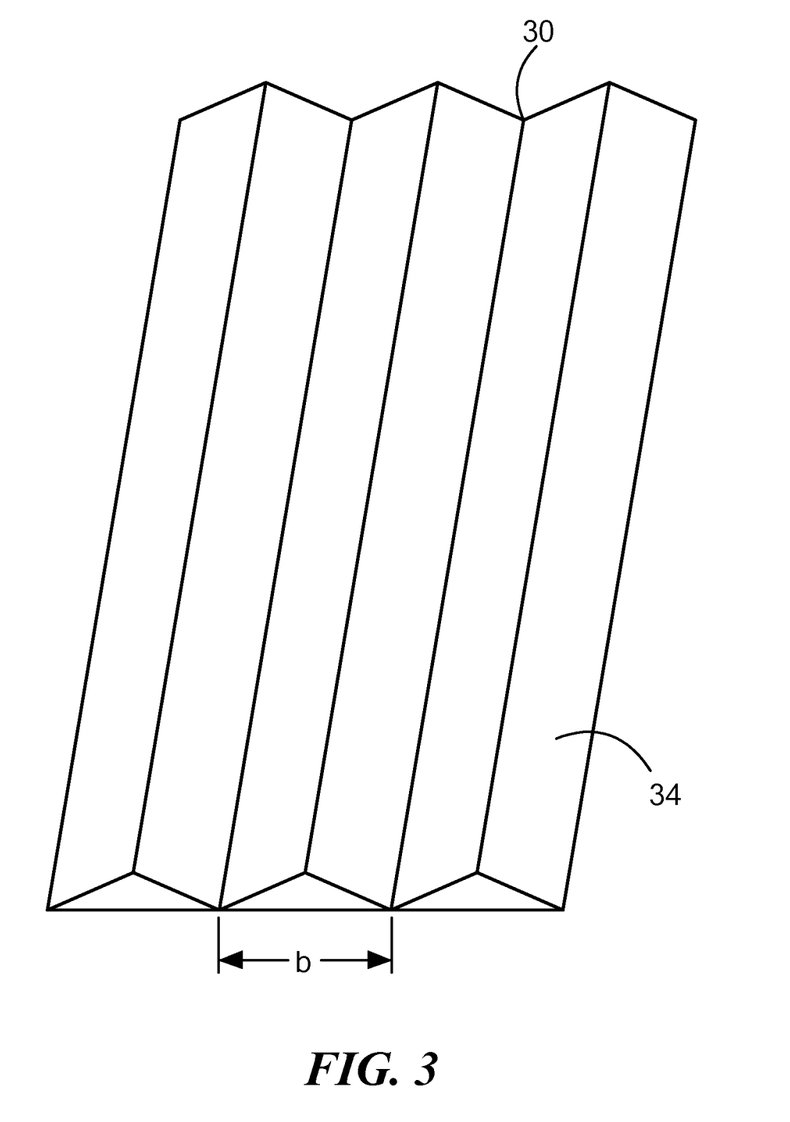
FIG. 3 is a front perspective view of another embodiment of surface modifications of the controller shown in FIG. 1 in accordance with the principles of the present application.

Referring now to FIG. 3, in another configuration, the exterior surface 30 of the shell 28 of the housing 24 defines a plurality of corrugations 34 along a portion or the entirety of the exterior surface 30. The corrugations 34 may be disposed on the exterior surface 30 in the same or similar manner as described above with respect to the embodiment shown in FIG. 2. For example, the corrugations 34 may define a triangular cross-section as shown in FIG. 3, which each corrugation 34 being contiguous with an adjacent corrugation 34. In one configuration, the height (a) of each corrugation 34 is 2 mm and a one-half of base (b) of each corrugation 34 is 1.15 mm and the angle (θ) defined by each triangle is 60°, the surface area of the exterior surface 30 is increased by 100% which increases the heat dissipation rate from the controller 12. In other configurations, the triangle cross-sectional of any of the corrugations 34 may define any height (a), base (b), or angle (θ).

Figure 4:
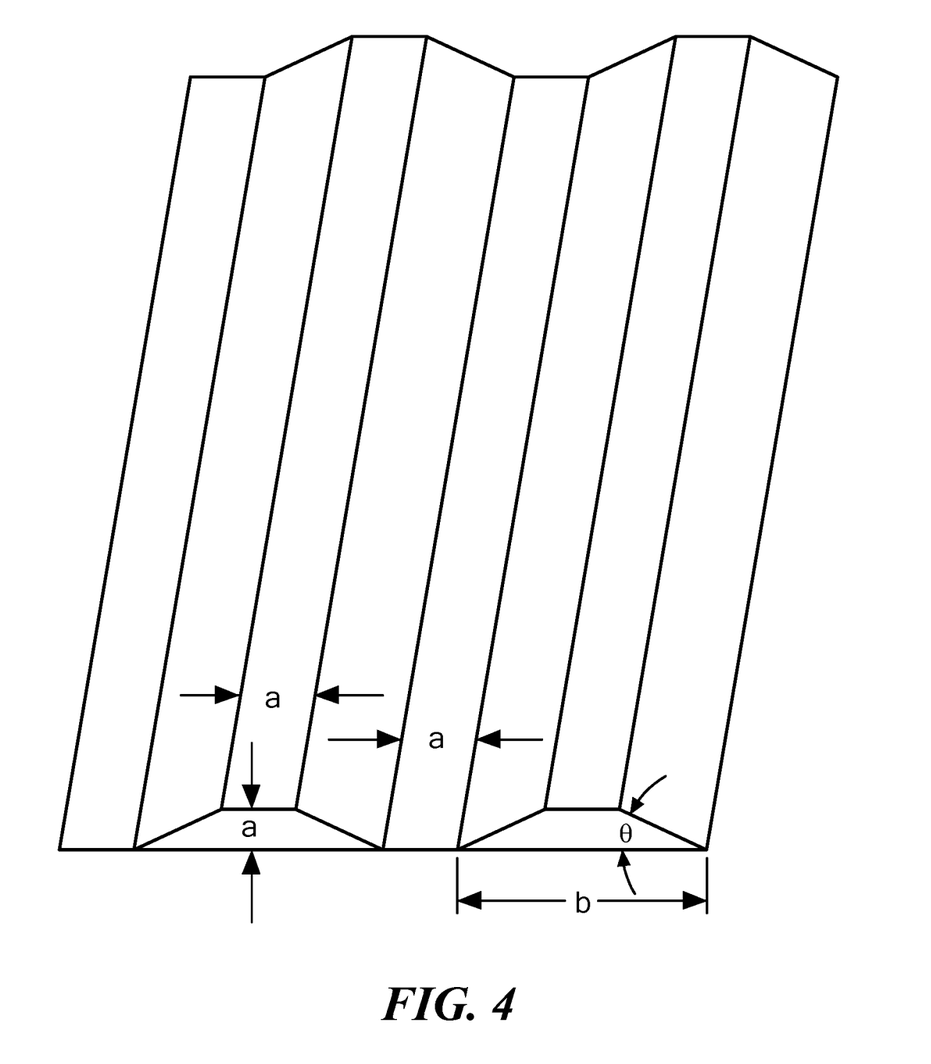
FIG. 4 is a front perspective view of another embodiment of surface modifications of the controller shown in FIG. 1 in accordance with the principles of the present application.

Referring now to FIG. 4, in another configuration, the corrugations 34 may be spaced a distance apart from an adjacent corrugation 34 and define a trapezoidal cross-section. In one configuration the angle (θ) defined by the intersection between each leg and the larger base of each trapezoid is 45°, and the smaller base defines a height (a) equal to one-half the base (b), which is also equal to the distance between each corrugation 34. In such a configuration in which the width (w) is equal to 8*(a), the increase in surface area by two adjacent corrugations 34 is 21%. Such a configuration is merely exemplary, and any number of corrugations 34 and distance between each corrugation 34 is contemplated.

Figure 5:
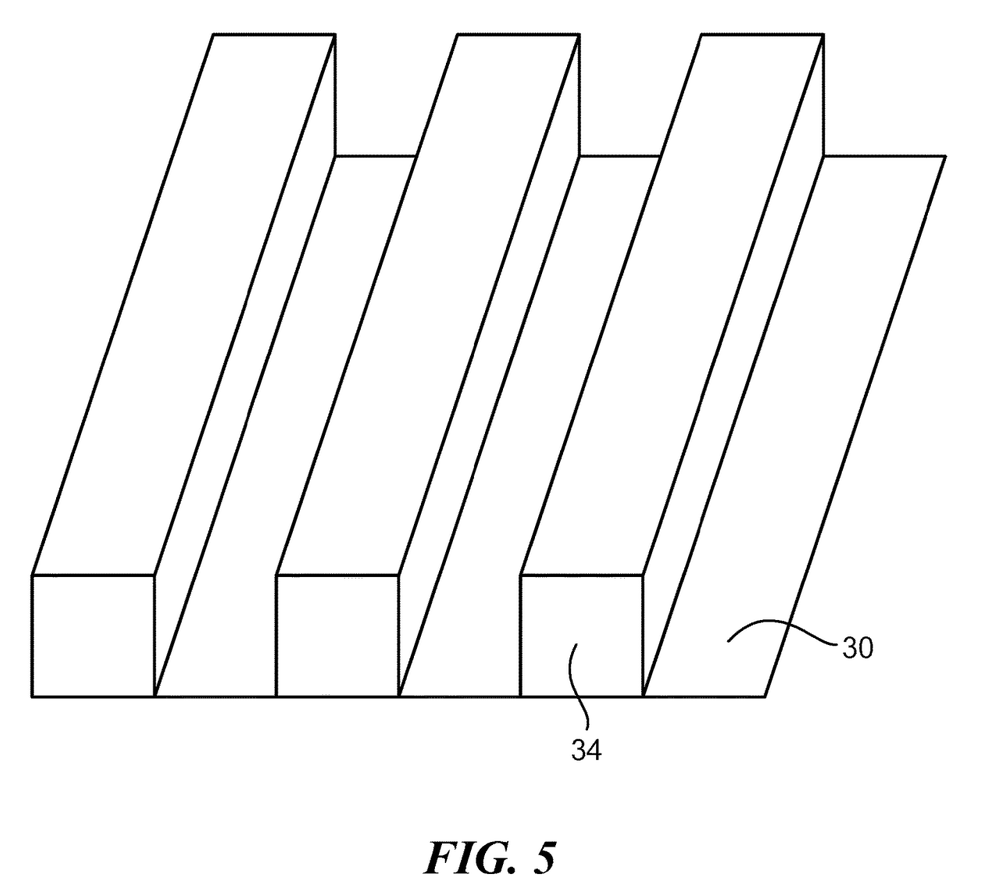
FIG. 5 is a front perspective view of another embodiment of surface modifications of the controller shown in FIG. 1 in accordance with the principles of the present application.

Referring now to FIG. 5, in another configuration, the corrugations 34 define a square or rectangular shape and may be disposed on a portion of the exterior surface 30 or the entirety of the exterior surface 30. Similar to the configuration shown in FIG. 4, the corrugations 34 may be spaced at an equal distance apart from each other and further define a square cross-section. In other configurations, the corrugations 34 may be sinusoidal or otherwise undulating in shape.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A controller for an implantable medical device, the controller comprising:
a housing sized and configured to be received within a patient, the housing comprising a thermally conductive shell defining an exterior surface, at least a portion of the exterior surface of the thermally conductive shell defining at least one from the group consisting of a plurality of corrugations and a plurality of protuberances.

2. The controller of claim 1, further including a battery enclosed within the housing, the battery being configured to power the implantable medical device when the controller is connected to the implantable medical device.

3. The controller of claim 1, wherein the thermally conductive shell defines the plurality of protuberances, and wherein the plurality of protuberances is disposed on an entirety of the exterior surface of the thermally conductive shell.

4. The controller of claim 3, wherein each protuberance of the plurality of protuberances defines a protuberance height and a protuberance diameter, and wherein a ratio of protuberance diameter to protuberance height is at least 2:1.

5. The controller of claim 4, wherein a density of the plurality of protuberances on the exterior surface of the thermally conductive shell is 3.25 protuberances per $cm^2$.

6. The controller of claim 5, wherein each protuberance of the plurality of protuberances is spaced apart from every other protuberance of the plurality of protuberances.

7. The controller of claim 1, wherein the thermally conductive shell defines the plurality of corrugations, and wherein the plurality of corrugations is disposed on an entirety of the exterior surface of the thermally conductive shell.

8. The controller of claim 7, wherein each corrugation of the plurality of corrugations defines a cross-sectional shape of one from the group consisting of square, rectangular, triangular, and trapezoidal.

9. The controller of claim 8, wherein each corrugation of the plurality of corrugations is contiguous with an adjacent corrugation of the plurality of corrugations.

10. The controller of claim 8, wherein each corrugation of the plurality of corrugations is spaced apart from every other corrugation of the plurality of corrugations.

11. A controller for an implantable blood pump, the controller comprising:
a housing sized and configured to be received within a patient, the housing comprising a thermally conductive shell defining an exterior surface, at least a portion of the exterior surface of the thermally conductive shell defining at least one from the group consisting of a plurality of corrugations and a plurality of protuberances; and
a battery disposed within the housing, the battery being configured to power the implantable blood pump when the controller is connected to the implantable blood pump;
the housing being configured to electrically couple with an implantable transcutaneous energy transfer coil, the transcutaneous energy transfer coil being configured to power the battery.

12. The controller of claim 11, wherein the thermally conductive shell defines the plurality of protuberances, and wherein the plurality of protuberances is disposed on an entirety of the exterior surface of the thermally conductive shell.

13. The controller of claim 12, wherein each protuberance of the plurality of protuberances defines a protuberance height and a protuberance diameter, and wherein a ratio of protuberance diameter to protuberance height is at least 2:1.

14. The controller of claim 13, wherein a density of the plurality of protuberances on the exterior surface of the thermally conductive shell is 3.25 protuberances per cm².

15. The controller of claim 14, wherein each protuberance of the plurality of protuberances is spaced apart from every other protuberance of the plurality of protuberances.

16. The controller of claim 11, wherein the thermally conductive shell defines the plurality of corrugations, and wherein the plurality of corrugations is disposed on an entirety of the exterior surface of the thermally conductive shell.

17. The controller of claim 16, wherein each corrugation of the plurality of corrugations defines a cross-sectional shape of one from the group consisting of square, rectangular, triangular, and trapezoidal.

18. The controller of claim 17, wherein each corrugation of the plurality of corrugations is contiguous with an adjacent corrugation of the plurality of corrugations.

19. The controller of claim 11, wherein the thermally conductive shell defines the plurality of protuberances, and wherein the plurality of protuberances is evenly spaced about the exterior surface.

20. A controller for an implantable blood pump, the controller comprising:
   a unitary housing sized and configured to be received within a patient, the housing comprising a thermally conductive metallic shell defining an exterior surface, an entirety of the exterior surface of the thermally conductive metallic shell defining a plurality of protuberances evenly spaced about the exterior surface, each protuberance of the plurality of protuberances being spaced apart from another protuberance of the plurality of protuberances, wherein each protuberance of the plurality of protuberances defines a protuberance height and a protuberance diameter, and wherein a ratio of protuberance diameter to protuberance height is at least 2:1;
   a battery disposed within the housing, the battery being configured to power the implantable blood pump when the controller to the implantable blood pump; and
   the housing being configured to electrically couple with an implantable transcutaneous energy transfer coil, the transcutaneous energy transfer coil being configured to power the battery.

* * * * *